(12) United States Patent
Vetter et al.

(10) Patent No.: US 9,687,162 B2
(45) Date of Patent: Jun. 27, 2017

(54) MONITORING DEVICE AND METHOD FOR ESTIMATING BLOOD CONSTITUENT CONCENTRATION FOR TISSUES WITH LOW PERFUSION

(75) Inventors: Rolf Vetter, Cottens (CH); Leopoldo Rossini, Camorino (CH); Andrea Ridolfi, Bern (CH); Josep Sola i Caros, Corcelles (CH); Marc Correvon, Cornaux (CH)

(73) Assignee: CSEM CENTRE SUISSE D'ELECTRONIQUE ET DE MICROTECHNIQUE SA—RECHERCHE ET DÉVELOPPEMENT, Neuchâtel (CH)

( * ) Notice: Subject to any disclaimer, the term of this patent is extended or adjusted under 35 U.S.C. 154(b) by 0 days.

(21) Appl. No.: 13/406,691

(22) Filed: Feb. 28, 2012

(65) Prior Publication Data

US 2012/0190948 A1 Jul. 26, 2012

Related U.S. Application Data

(63) Continuation of application No. PCT/EP2010/059616, filed on Jul. 6, 2010.

(Continued)

(51) Int. Cl.
*A61B 5/1455* (2006.01)
*A61B 5/024* (2006.01)
(Continued)

(52) U.S. Cl.
CPC ...... *A61B 5/02405* (2013.01); *A61B 5/14552* (2013.01); *A61B 5/7221* (2013.01);
(Continued)

(58) Field of Classification Search
CPC .............. A61B 5/1455; A61B 5/14551; A61B 5/0002; A61B 5/0059; A61B 5/024; A61B 5/14552
USPC ....... 600/300, 309, 322, 323, 324, 326, 336, 600/340, 473, 476, 509; 356/41
See application file for complete search history.

(56) References Cited

U.S. PATENT DOCUMENTS 5,827,195 A * 10/1998 Lander .......................... 600/509
6,334,065 B1 * 12/2001 Al-Ali et al. .................. 600/323
(Continued)

OTHER PUBLICATIONS

Vetter R et al: "Frequency Doman Sp02 Estimation Based on Multichannel Photoplethysmographic Measurements at the Sternum", International Federation for Medical and Biological Engineering, vol. 25, No. 4, Sep. 7, 2009, p. 2-7.

(Continued)

*Primary Examiner* — Eric Winakur
*Assistant Examiner* — Chu Chuan (JJ) Liu
(74) *Attorney, Agent, or Firm* — Pearne & Gordon LLP (57) ABSTRACT

The present disclosure relates to a method for estimating blood constituent concentration of a user under low perfusion conditions using a spectrophotometry-based monitoring device; the method comprising: measuring a plurality of photoplethysmographic (PPG) signals; measuring a cardio-synchronous (CV) signal; detecting an instantaneous heart rate and determining a heart rate variability from the CV signal; selecting reliable projected PPG signals; estimating a value of said blood constituent concentration from the magnitude of said reliable projected PPG signals. The disclosed method requires diminished computational load compared to conventional methods based on frequency domain approach as FFT or DCT. The disclosure also pertains to a monitoring device for estimating blood constituent concentration in tissue under low perfusion of a user.

22 Claims, 5 Drawing Sheets

Related U.S. Application Data (60) Provisional application No. 61/272,238, filed on Sep. 3, 2009.

(51) Int. Cl.
 *A61B 5/0205* (2006.01)
 *A61B 5/0245* (2006.01)
 *A61B 5/00* (2006.01)

(52) U.S. Cl.
 CPC .......... *A61B 5/0205* (2013.01); *A61B 5/0245* (2013.01); *A61B 5/02416* (2013.01); *A61B 5/721* (2013.01); *A61B 5/7257* (2013.01); *A61B 2562/0219* (2013.01); *A61B 2562/0233* (2013.01); *A61B 2562/046* (2013.01)

(56) References Cited

U.S. PATENT DOCUMENTS

| | | | |
|---|---|---|---|
| 6,879,850 B2 * | 4/2005 | Kimball | 600/336 |
| 2003/0065269 A1 | 4/2003 | Vetter et al. | |
| 2006/0211924 A1 | 9/2006 | Dalke et al. | |

OTHER PUBLICATIONS

A. Ridolfi: "Biomedical Processing and Portable Physiological Monitoring Devices", Jun. 13, 2009, pp. FRP-41; retrieved from Internet: http://www.dcc.fc.up.pt/{mcoimbra/lectures/PSI_0809/PSI_2009_ARidolfi.pdf.

Miguel Tavares Coimbra: "Processamento de Sinal e Imagem (Mest. Inf. Medica) Sep. 2008"; Online, pp. 1-2, retrieved from internet: http://www.dcc.fc.up.pt/{mcoimbra/lectures/psi_0809.html—the document validates the publication date of A. Ridolfi: Biomedical Processing and Portable Physiological Monitoring Devices.

Frans M Coetzee et al.: "Noise-Resistant Pulse Oximetry Using a Synthetic Reference Signal", IEEE Transactions on Biomedical Enginering, vol. 47, No. 8, Aug. 1, 2000, pp. 1018-1026.

International Search Report for PCT/EP2010/059616 dated Nov. 19, 2010.

Horecker, B. L., "The Absorption Spectra of Hemoglobin and Its Derivatives in the Visible and Near Infra-Red Regions", J. Biol. Chem. 1943, 148:173-183.

Mendelson, Yitzhak, "Pulse Oximetry: Theory and Applications for Noninvasive Monitoring", Clinical Chemistry, 1992, p. 1601-1607, vol. 38, No. 9.

* cited by examiner

MONITORING DEVICE AND METHOD FOR ESTIMATING BLOOD CONSTITUENT CONCENTRATION FOR TISSUES WITH LOW PERFUSION

REFERENCE DATA

This application claims priority to U.S. provisional patent application Ser. No. 61/272,238, filed on Sep. 3, 2009. Priority to the provisional application is expressly claimed, and the disclosure of which is hereby incorporated herein by reference in its entirety and for all purposes.

FIELD OF THE INVENTION

The present disclosure relates to a method for estimating blood constituent concentration of a user under low perfusion conditions using a spectrophotometry-based monitoring device.

BACKGROUND

Pulse oximetry is a common, non-invasive method used in clinical environments to determine arterial oxygen (de-) saturation. Introduced in 1983 to permit accurate and fast assessment of oxygen delivery, it is recognized worldwide as the standard of care inanaesthesiology and is widely used in intensive care, operating rooms, emergency, patient transport, general wards, birth and delivery, neonatal care, sleep laboratories, home care, veterinary medicine and aerospace. Even more, pulse oximetry provides information not only for the blood oxygen saturation ($SpO_2$), but also for heart rate and local vascular irrigation. In commercial devices, either LEDs or LASERs generate the light to be injected into the skin. The backscattered light is then collected by a photo detector (e.g. aphotodiode). These two elements can be placed either side by side on the surface of the tissue, or on each sides of the tissue leading to two pulse oximetry techniques: reflectance and transmittance. Most $SpO_2$ sensors use the fingertip or more rarely, the toe, as the measurement site. The reason is that at these locations, the vascular bed is dense. Besides, the body is not too thick at the finger or the toe; transmission photoplethysmography (PPG) is possible, which results in better accuracy than reflectance PPG. The earlobe is also sometimes used, although problems of perfusion variations have been reported. Finally, reflectance PPG is used mostly on the forehead, because of the reflectance of the skull and the relative stability with respect to motion artifacts. However, the pulsation signal is about ten times weaker. Besides, accuracy problems have been reported.

Commercially available $SpO_2$ sensors products are incompatible with comfortable and non-obtrusive long-term monitoring because they are either inconvenient and cumbersome to wear while performing activities like running, cycling or other outdoor activities (for example at the fingertip) or their accuracy and reliability are limited (as for example for the earlobe and the forehead).

The information conveying part in pulse oximetry is the so called ratio of ratios ($R_{OS}$), which is the ratio of AC and DC components of a red signal divided by the ratio of AC and DC components of an infrared signal. From the signal processing point of view, the most crucial task leading to an accurate $SpO_2$ estimation is therefore the accurate assessment of AC and DC components of the photoplethysmographic signals. Conventionally, this is achieved either in the time domain by extrema location or template matching or in the frequency domain by extraction of the magnitude of specific spectral components [1]. Time domain methods, even in their most advanced implementation, currently based on weighted moving average technique, give a precision of no better than 2%. In contrast, frequency domain methods based on fast Fourier or cosine transform were identified as potentially superior, as described in reference 1: Webster J G, Design of Pulse Oximeters, Medical Science Series, IOP Publishing (1997). Moreover, in highly noisy environments it has been shown in numerous studies of applied signal processing that robust extraction of efficient and salient features of multidimensional times series is often related to an adequate attenuation of harmful noise contributions in a dual domain, such as, for example, the frequency domain or the domain spanned by the principal or independent component of the observed signals (see reference 2: Virag N, Sutton R, Vetter R, Markowitz T, Erickson M (2007), Prediction of vasovagal syncope from heart rate and blood pressure trend and variability: Experience in 1,155 patients. Heart Rhythm, vol. 4, No. 11, pp. 1377-1382).

The use of ECG signal, or more generally the heart beat information, brings along another advantage in processing noisy PPG signal due to low perfusion. Indeed, in order to improve the noise robustness of pulse oximetry under low perfusion, methods have been proposed which process PPG signals in the time domain in synchronization with ECG (see reference 1).

Known methods for monitoring $SpO_2$ based on frequency domain, such as FFT or DCT, typically require a high computational load. Moreover, the signal is analyzed over a window that is constant such that the analyzed signal can be more or less reliable depending on the possible artifacts and the intrinsic heart rate variability, resulting in a less reliable $SpO_2$ estimated value.

SUMMARY

The present application discloses a spectrophotometry-based monitoring method which overcomes at least some limitations of the prior art.

According to the embodiments, a method for estimating blood constituent concentration of a user under low perfusion conditions using a spectrophotometry-based monitoring device comprising a multichannel sensor formed of a plurality of channels, and a cardiovascular sensor; can comprise: measuring a plurality of photoplethysmographic (PPG) signals, each PPG signal being measured by one of a plurality of channels; measuring a cardio-synchronous (CV) signal by using the cardiovascular sensor; detecting a instantaneous heart rate and determining a heart rate variability from the CV signal; for each detected heart rate, projecting the measured PPG signals multiplied by a window function on a principal frequency component, and selecting reliable projected PPG signals; and estimating a value of said blood constituent concentration from the magnitude of said reliable projected PPG signals selected over a predetermined time period; characterized in that said window function has a window length which is adjusted at each detected heart rate according to the determined heart rate variability; and in that the frequency of said principal frequency component is estimated by averaging the heart rate over the window length.

In an embodiment, said blood constituent concentration can comprise oxyhemoglobin, reduced-hemoglobin, carboxyhemoglobin, methemoglobin, or a combination of any of them.

In another embodiment, the principal frequency component can be a harmonic component with its phase being determined by the time instant of the instantaneous heart rate and with its frequency being determined by the averaged heart rate.

In yet another embodiment, the principal frequency component can be a wavetable oscillator with its phase being determined by the instantaneous heart rate and with its frequency being determined by the averaged heart rate.

In yet another embodiment, said averaging the heart rate can comprise determining the mean heart rate value of heart rate detected prior to the instantaneous heart rate, over the whole window length.

In yet another embodiment, said selecting reliable projected PPG signals can comprise selecting projected PPG signals having a predetermined magnitude and a predetermined phase and/or coherence between the PPG signals and the principal frequency component.

In yet another embodiment, said predetermined coherence can be equal or above 0.7.

In yet another embodiment, the monitoring device can further comprise a motion sensor for measuring a motion signal, and the method can further comprise extracting a motion frequency from the motion signal.

In yet another embodiment, the window function can be designed according to the extracted motion frequency.

In yet another embodiment, for the motion artifacts being smaller than large-band background noise, the window function can have maximal attenuation of lateral lobes, and the window function can be a Hanning window or a Kaiser window.

In yet another embodiment, for the motion artifacts being larger than large-band background noise, the window function yields an equivalent frequency response having zeros at the motion frequency and its harmonics, and the window function is a rectangular window.

The disclosure further concerns a method for the estimation of SpO2 in tissue under low perfusion including:

the measure of the PPG signals using a multichannel sensor, an ECG sensor and inertial sensors such as accelerometers;

estimating the magnitude, phase and coherence of the PPG signals ECG guided principal frequency component projection;

selecting reliable projections of PPG signals; and estimating SpO2 value based on the reliable PPG signal magnitude.

The reliability of a given projection of PPG signals can be obtained from the phase and/or magnitude and/or coherence between the projection of the PPG signal and the ECG guided principal frequency component. In a further embodiment, the reliability may also be obtained from the phase and/or coherence between the PPG signals.

The projection length can be determined with respect to the noise environment:

if regular harmonic noise is predominant such as the one generated by regular harmonic movements, the projection length and window type are chosen in order to place zeros of the frequency response of the window at the absolute value of the difference between heart rate and movement frequency;

in the presence of large band background noise the projection length and window type are chosen such as to provide a frequency response of the window with a bandwidth corresponding to the heart rate variability measured on the ECG over the same window length in the past.

The principal frequency component is a harmonic signal such as the complex exponential, its phase being determined by the corresponding instantaneous R-wave location on the ECG and its frequency being determined by the mean heart rate measured on the ECG over the same window length in the past.

In a further embodiment, the principal frequency component is a wavetable oscillator, its phase being determined by the corresponding instantaneous R-wave location on the ECG and its frequency being determined by the mean heart rate measured on the ECG over the same window length in the past. The fundamental wavelet of the wavetable oscillator being updated in function of reliable PPG waveforms.

The disclosure also pertains to a monitoring device for estimating blood constituent concentration in tissue under low perfusion of a user using the method disclosed herein and comprising the disclosed multichannel sensor, and a cardiovascular sensor for delivering a cardio-synchronous (CV) signal.

In an embodiment, the monitoring device can further comprise a motion sensor for measuring a motion signal.

In another embodiment, each of said plurality of channels can comprise an emitter containing a first and second radiation source emitting at the red and infrared wavelengths, respectively, and a receiver for receiving optical radiation emitted by the emitter.

In yet another embodiment, said cardiovascular sensor can be an ECG sensor and the CV signal is a surface ECG signal, or an ECG sensor and the CV signal is a PPG signal.

The method disclosed herein provides reliable estimation of the blood constituent concentration even for tissues under very poor perfusion. This is mainly due to fact that detection of the time instant of heart beat and estimation of the instantaneous heart rate may be performed with high reliability and accuracy on ECG and projection on according principal frequency component provides highest noise reduction if the projection length is chosen optimally with respect to heart rate variability and noise in PPG signals. The disclosed method requires computational load that is highly diminished compared to conventional methods based on frequency domain approach as FFT or DCT.

BRIEF DESCRIPTION OF THE DRAWINGS

The preferred embodiments will be better understood with the aid of the description of an embodiment given by way of example and illustrated by the figures, in which.

DETAILED DESCRIPTION OF THE PREFERRED EMBODIMENTS

Figure 2:
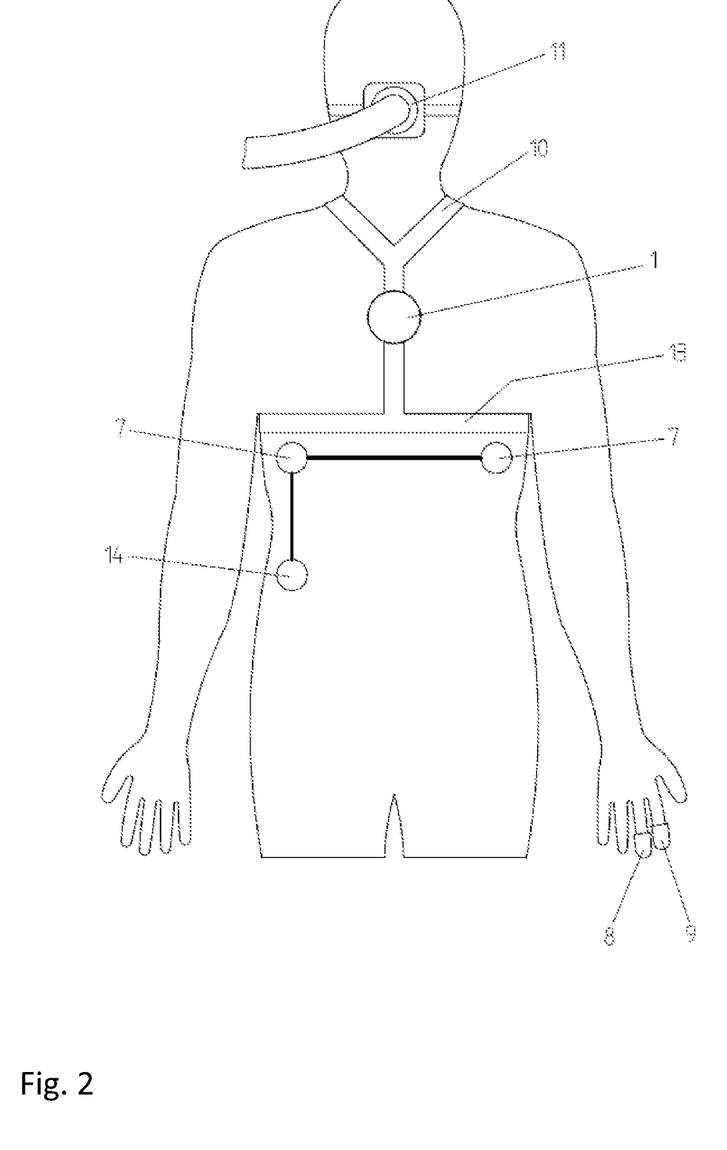
FIG. 2 illustrates schematically a monitoring device comprising the multichannel sensor, according to an embodiment.

FIG. 2 illustrates schematically a spectrophotometry-based monitoring device according to an embodiment. The monitoring device comprises a multichannel sensor 1, containing a plurality of photoplethysmographic (PPG) sensor channels, and fitted in a strap band 10 such as to be located in contact with the user's skin, in the sternum area. Such placement is comfortable and non obtrusive for long-term monitoring while performing activities like running, cycling or other outdoor activities. Other placements of the multichannel sensor 1 are however possible, for example, on a wrist strap, on a forehead-band, or on any suitable location within the scope of the embodiments. An advantage of the disclosed monitoring device setup and measurement method is that the multichannel sensor 1 can be located in an area having low perfusion while providing reliable estimation of constituents in blood such as blood oxygen saturation ($SpO_2$) as will be described below.

Figure 1:
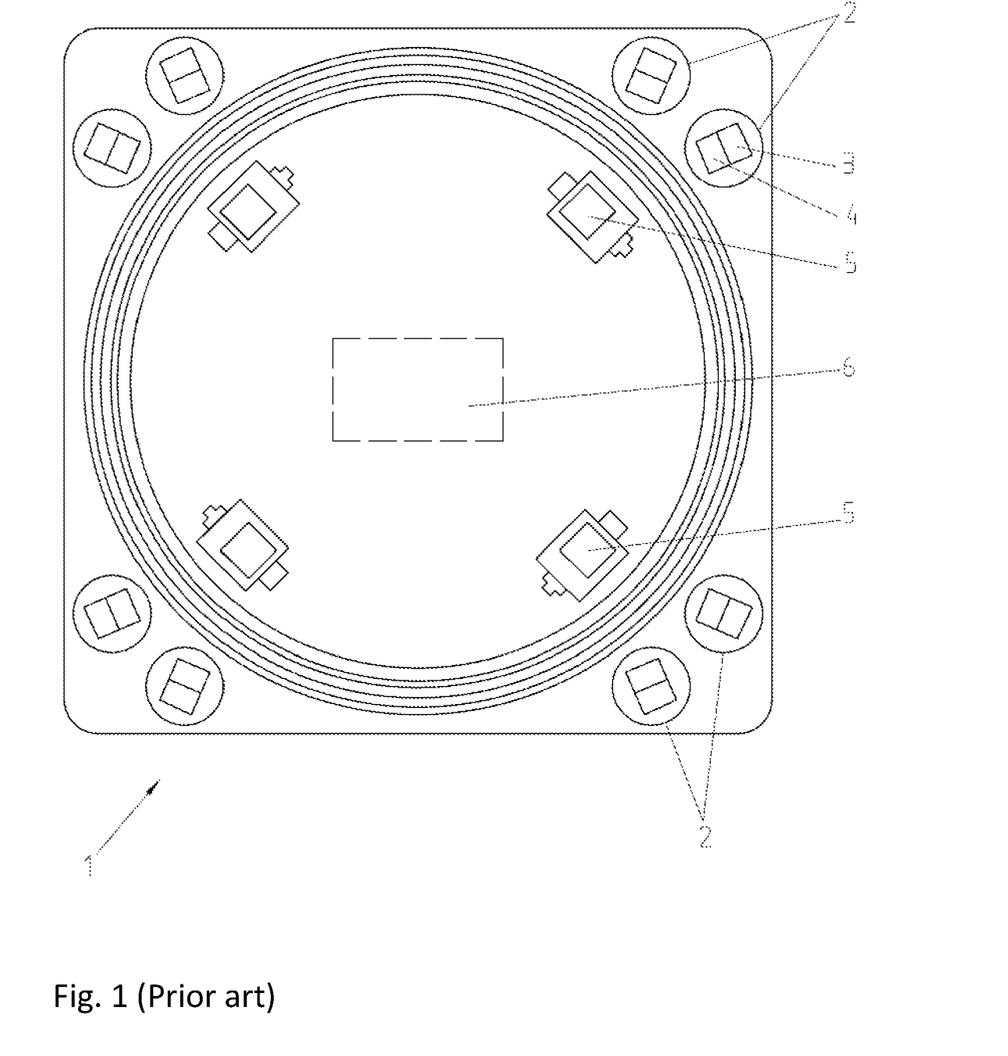
FIG. 1 represents schematically a multichannel sensor according to an embodiment.

The multichannel sensor 1 is represented schematically FIG. 1, according to an embodiment. The multichannel sensor 1 comprises eight equally radially disposed individual PPG sensor channels. The multichannel sensor 1 can measure a plurality of PPG signals, each PPG signal being measured by one of the channels 2, 5. Each PPG sensor channel is formed from an emitter 2 comprising a first radiation source 3 emitting at the red wavelengths and a second radiation source 4 emitting at the infrared wavelengths. The first and second light sources 3, 4 can be LEDs, preferably emitting at 660 nm and 940 nm, respectively. Each PPG sensor channel also comprises a receiver 5, such as a photodetector, for receiving the optical radiation emitted by the emitter 2 and transmitted through the skin tissue. The receiver 5 is connected to an analog-to-digital converter (ADC) module (not represented) delivering corresponding measured PPG signals. In the example of FIG. 1, the multichannel sensor 1 contains four equally radially spaced receivers 5, each receiver 5 being used to receive the PPG signals transmitted from two adjacent emitters 2. Other numbers and arrangements of the emitters 2 and receivers 5 are also possible as long as it provides sufficient spatial diversity in order to remove artifacts due to tissue inhomogeneities. Spatial diversity allows one to overcome poor PPG signal quality related to inhomogeneous and poor subcutaneous blood flow, to attenuatenon-correlated measurement noise in the different channel, as well as reduce artifacts related to movements which may not be recorded by an accelerometer. However, this requires a more sophisticated signal processing.

In an embodiment, the multichannel sensor 1 further comprises a motion sensor 6 for measuring a motion signal representative of the user's movements. As schematically shown in FIG. 1, the motion sensor 6 is placed within the multichannel sensor 1, possibly forming an integrated sensor comprising the multichannel sensor 1 and the motion sensor 6. In this configuration, the motion signal is better correlated with the measured multichannel sensor 1 signal than if the motion sensor 6 is placed further from the multichannel sensor 1. Moreover, the placement of the multichannel sensor 1 on the sternum is advantageous since it approximates essentially gravity center based accelerometer measurement on the user. The motion sensor 6 can comprise an ADC module (not shown) outputting acquired motion signals.

The motion sensor 6 is preferably a MEMS-based three dimensional accelerometer adapted to deliver an acceleration signal along three axes, as described in U.S. Pat. No. 7,018,338 by the present applicant. It will however be appreciated that other types of accelerometers or motion detecting devices can be used provided they deliver a reliable measure of motion. For example, the motion sensor 6 could be a gyro-sensor of any suitable technology incorporating a one or multi-dimensional accelerometer, or a rotating or vibrating element.

In the example of FIG. 2, the monitoring device further comprises a cardiovascular sensor for measuring a cardiosynchronous (CV) signal. The cardiovascular sensor is an ECG sensor and contains two signal ECG electrodes 7 being fixed on a chest band 13, connected to the strap band 10, such as to be in contact with the user's skin. The ECG sensor also comprises an ECG ground electrode shown by the numeral 14 in FIG. 1. ECG electrodes 7, 14 are preferably widely spaced across the patient's body. Other arrangements of the ECG electrodes are also possible. Flexible ECG electrodes, for example such as described in U.S. patent application Ser. No. 2006/0142654, can be integrated into the chest band and/or the strap tissue or into a garment fabric. The ECG electrodes can be connected to a comparator (not shown) for determining a difference value between the measured electric potentials at the different ECG electrode locations. The ECG sensor can comprise more than two signal ECG electrodes 7. Moreover, the ECG sensor can comprise an ADC module (also not shown) outputting the acquired measured CV signal.

In another embodiment, the cardiovascular sensor is a PPG-based CV sensor and the CV signal is a PPG-based CV sensor signal. Here, the multichannel sensor 1 can be utilized for measuring the PPG-based CV sensor signal, or the PPG-based CV sensor can be an additional PPG-based sensor (not shown). Alternatively, the cardiovascular sensor can be based on impedance cardiography, ultrasound, or any other measurement device adapted to provide a reliable CV signal from the user.

The measuring the CV signal and the plurality of PPG signals can comprise acquiring the CV and PPG signal with a predetermined sampling rate. The sampling rate is typically comprised between 20 and 30 Hz. In the following text, the expressions "measured CV signal" or "measured PPG signal" and "CV sample" or "PPG sample" will be used indifferently.

In an embodiment, the respective ADC modules of the PPG sensor channels 2, 5, motion sensor 6, and ECG sensor 7, 14 further comprise a signal filtering and shaping device (not shown). The respective ADC modules can be formed from a single ADC module placed in the strap band 10 or chest band 13. Filtering of the measured analog PPG, motion, and CV signals can be performed by means of an analog low-pass filter whose band is of 10 Hz for the PPG signals and 50 Hz for the ECG and motion signals, for example. The measured signals are then transferred to a signal processing module (not shown).Eliminating artifacts due to movements of the user in the PPG and CV signals can be performed in the signal processing module by using the motion signal delivered by the motion sensor 6. Such processing is described in more details in the European patent application No. 1297784 and U.S. Pat. No. 7,175,601, both by the present applicant. A battery (also not shown) can also be placed in one of the bands 10, 13 to power the multichannel sensor 1 and ECG sensor 7, 14. The processing module can be an adequately programmed digital signal processor or DSP or a general purpose microcontroller (not represented). The measured PPG, motion, and CV signals can be transferred to the signal processing module through a cable (not shown) or wirelessly.

In yet another embodiment not represented, the multichannel sensor 1 and/or ECG sensor 7, 14 can include an embedded signal processor or other type of dedicated processors for performing any desired processing of the measured PPG, CV or motion signals, prior to outputting signals to the signal processing module.

Figure 3:
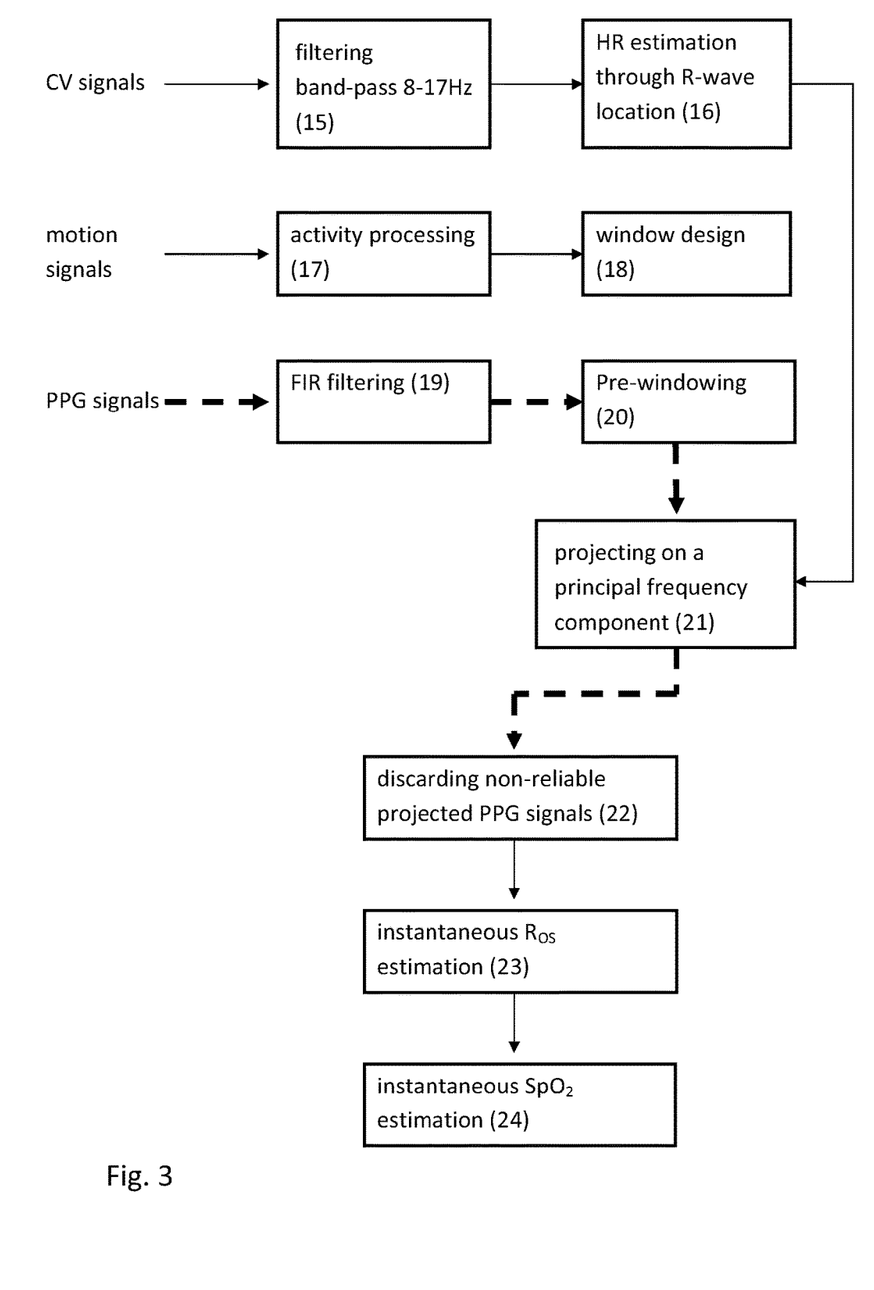
FIG. 3 is a flow chart illustrating a method for estimating a value of gas concentration in blood under low perfusion conditions using the monitoring device.

A method for estimating a value of gas concentration in blood under low perfusion conditions using the monitoring device disclosed herein is diagrammatically shown in FIG. 3 according to an embodiment. The method comprises the steps of:

measuring the CV signal by using the ECG sensor 7, 14;

measuring the plurality of PPG signals, each PPG signal being measured by one of the channels 2, 5;

detecting heart beats, or an instantaneous heart rate, and determining a heart rate variability from the measured CV signal (numeral 16 in FIG. 3);

for each detected heart rate, projecting the measured PPG signals multiplied by a window function on a principal frequency component (numeral 21 in FIG. 3), and selecting reliable projected PPG signals (numeral 22 in FIG. 3); and estimating a $SpO_2$ value from the magnitude of said reliable projected PPG signals selected over a predetermined measurement time period (numeral 24 in FIG. 3).

The method can further comprise a step of filtering the measured PPG and CV signals. This step is shown respectively by numerals 15 and 19 in FIG. 3. Filtering of the measured CV signals can be performed by using a numerical finite length band-pass filter, preferably using a band-pass in the frequency range comprised between 15 and 30 Hz. Filtering the measured PPG signals can be performed by using a numerical band-pass filter, such as a finite impulse response (FIR) filter.

Heart beats can be detected from the CV signals using the maximum of the R-Wave. The instantaneous heart rate can then be determined from the time difference between the R-R intervals, between the two adjacent R-Wave maxima. The instantaneous heart rate variability, then, corresponds to the maximal variation of the R-R intervals over the analysis window length defined below.

In an embodiment, the projecting of the PPG samples, or the instantaneous projecting of the PPG samples, for each detected heart rate is obtained by using Equation 1:

$$PPG_{proj}(n) = \sum_{l=-w_{len}/2}^{w_{len}/2} w(l) PPG(k_{HR(n)} - w_{len}/2 - l) PC(l) \quad \text{(Equation 1)},$$

where $PPG_{proj(n)}$ corresponds to the projected PPG sample for the $n^{th}$ heart rate detected in the CV signal at a time instant $t_{R(n)}$ of the maximum of the associated R-wave and which corresponds to a sample in the PPG signal, w(1) is the window function, and a window length of the projection. The principal frequency component PC(1) phase adjusted to the $n^{th}$ heart beat is defined by Equation 2:

$$PC(l) = e^{j2\pi f_c(k_{HR}(k) - w_{len}/2 - l)} \text{ with } -w_{len}/2 \leq l \leq w_{len}/2 \quad \text{(Equation 2)},$$

where $f_c$ is the mean heart rate over the window length as defined in the procedure below, normalized with respect to the sampling frequency of the PPG signals.

The window function can be designed, for example, from a rectangular, Hanning, Hamming, or Blackman window function. The step of designing the window function is represented by the numeral 20 in FIG. 3 and is described in more details below.

The window length can be optimally adjusted at each heart rate by a procedure taking into account the maximal heart rate variability over the window length comprising the steps of:

1. starting at instantaneous heart rate (detected from the R-Wave) and evaluating an associated RR interval using Equation 3:

$$RR(n) = t_{R(n)} - t_{R(n-1)} \quad \text{(Equation 3)},$$

where $t_{R(n)} - t_{R(n-1)}$ corresponds to the difference of time instant of the $n^{th}$ and $(n-1)^{th}$ heart rates;

2. setting iteration index i=1.

3. evaluating an equivalent bandwidth $B_{eq}(i)$ as in Equation 4:

$$B_{eq}(i) \quad \text{(Equation 4)},$$

where f is a function depending on a given window;

4. evaluating the RR interval with:

$$RR_{(n-i)} = t_{R(n-i)} - t_{R(n-i-1)} \quad \text{(Equation 5)};$$

5. evaluating the equivalent bandwidth as:

$$B_{eq}(i+1) = f(1/\Sigma_{0=0}^{i}) \quad \text{(Equation 6)};$$

6. and while:

$$\max([1/RR_{(n-i)}, \ldots, 1/RR_{(n)}]) - \min([1/RR_{(n-i)}, \ldots, 1/RR_{(n)}]) < B_{eq}(i+1) \quad \text{(Equation 7)},$$

incrementi and go to step 4.

At the end of this procedure the optimal window length $t_{win}$ can be determined by Equation 8:

$$t_{win} = \Sigma_{0=0}^{i-1} \quad \text{(Equation 8)},$$

which yields in samples:

$$w_{len} = t_{win} * (\text{PPG sampling frequency}) \quad \text{(Equation 9)},$$

and the mean heart rate $f_c$ is determined by:

$$f_c = \text{mean}([1/RR_{(n-i+1)}, \ldots, 1/RR_{(n)}]) \quad \text{(Equation 10)}.$$

Moreover, the time instant of the last $t_{R(n)}$ provides the trigger for the generation of the principal frequency component. In FIG. 3, bold dashed lines indicate the PPG signals measured from the multichannel sensor 1 with their associated information, such as coherence, phase, and magnitude of the principal frequency component projection.

In an embodiment corresponding to a simplest case, the principal frequency component is a harmonic component with its phase being determined by the R-wave location, or instantaneous heart rate, on the corresponding CV signal delivered by the ECG-based sensor 7, 14, and with its frequency being determined by the mean heart rate value. Here, the mean heart rate value can be determined from the heart rates detected over the whole window length (past heart rates), prior to the instantaneous heart rate.

In another embodiment, the principal frequency component is a wavetable oscillator with its phase being determined by the instantaneous heart beat, or R-wave location, on the corresponding CV signal delivered by the ECG-based sensor 7, 14, and with its frequency being determined from the instantaneous heart rate and the heart rates detected over the whole window length (past heart rates). The fundamental wavelet of the wavetable oscillator can be updated as a function of the reliable projected PPG signals. This technique can yield a more robust projection of the PPG signals.

In an embodiment, reliability of the PPG signals is determined from the magnitude of the projected PPG signals and the phase, and/or coherence between the PPG signals and the principal frequency component. More particularly, the maximum attenuation of the PPG signals by the tissue occurs during the cardiac systole phase of the cardiac cycle, starting substantially at the R-wave. Therefore, the phase between the R-wave triggered principal frequency component and the PPG signal should vary within given bounds which can be fixed for a given channel location.

Reliable projected PPG samples can then be selected from the instantaneous projected PPG signals having a predetermined magnitude and for a predetermined phase, and/or coherence between the PPG signals and the principal frequency component. Reliable projected PPG signals can be selected for projected PPG signals obtained during a measurement period extending over several heart beats on the past, based on the magnitude, phase and coherence values estimated for each of the projected PPG signals.

In an embodiment, the reliable projected PPG signals are selected based on the coherence between the PPG signals and the principal frequency component having a value equal or above 0.7. The magnitude of the projected PPG signal depends on the electronics used but should be above background noise, or noise floor, for example at least twice the noise floor, but not too large where it would correspond to movement artifacts. Moreover, the phase should be comprised between a value above zero and less than a maximal angle $\phi$ which depends mainly on the sensor location and the heart rate, resulting in a linear phase relationship determined by:

$$\phi = 2\pi f_c \delta t \qquad \text{(Equation 11)}$$

where $\delta t$ is the maximally elapsed time between the occurrence of the heart beat and PPG pulse wave at the sensor location, typically $\delta t$ may be in the range of 5 to 30 ms).

In an embodiment, the method further comprises a step of extracting a motion frequency of the motion artifacts of the user (shown by numeral 17 in FIG. 3), and determining an activity of the user, by using motion signals measured by the motion sensor 6. Motion artifacts of the user can comprise regular periodical movement artifact related to activities like, for example, running, cycling, walking, etc., or voluntary and involuntary (respiration) subject movements. A fundamental, or central, motion frequency can be extracted from the motion signals through one of the following technique comprising zero-crossing, parametric or non-parametric spectral estimation, autocorrelation, recurrence plots. Such central motion frequency is typically representative of to the most harmful regular noise contributions from motion artifacts.

The window function can then be optimally designed according to the estimated motion frequency, or relative importance of the level of large-band background noise and movement artifacts, and possibly along with the determined heart rate, and a maximal heart rate variability. This step is represented by numeral 18 in FIG. 3. The maximal heart rate variability can be determined as the maximal heart rate variation over the window length as processed in step 6 of the above procedure.

For example, in the absence of regular movement artifacts or in the case the movement artifacts are smaller than large-band background noise, the design criterion of the window function is the maximization of the signal-to-noise ratio (SNR) of the PPG signals with respect to large-band background noise. In these conditions, the window function should preferably have maximal attenuation of lateral lobes, and the window function can be, for example, a Hanning or Kaiser window. The equivalent projection bandwidth should be minimal but even though retain the main signal characteristics. In these conditions, the projection, or window length, can be determined by a frequency response of the window function having a bandwidth corresponding to the maximal heart rate variability, determined over the same window length.

In the case where movement artifacts are larger than large-band background noise, the window function is such as to yield an equivalent frequency response having its zeros at the frequency of harmful regular noise contributions due to regular movement artifacts, or central motion frequency. For example, a rectangular window can be chosen in the case harmonic movement artifacts are predominant and the difference between heart rate and motion frequency is very small.

Values of ratio of ratios ($R_{OS}$) are obtained from the principal frequency component of the reliable projected PPG signals at each heart beat (detected from R-wave) and for each channel of the multichannel sensor 1. Here $R_{OS}$ stands for the ratio of the magnitudes of projections of harmonic components at heart rate and 0 Hz of the PPG signals in the red wavelengths, divided by the ratio of magnitude of projections of harmonic components at heart rate and 0 Hz of the PPG signals in the infrared wavelengths. The $R_{OS}$ is evaluated from the magnitude of the projections of all channels. An instantaneous $R_{OS}$ estimation can then be determined by applying a statistical technique (for example mean, median, maximum likelihood) to a matrix comprising the $R_{OS}$ values obtained from the reliable projected PPG signals at each heart beat and for each channel, during the measurement time period extending over several heart beats on the past (numeral 23 in FIG. 3).

In a last step shown by numeral 24 in FIG. 3, an instantaneous $SpO_2$ estimation is obtained as in conventional pulse oximetry by Equation 12:

$$SpO_2(t) = a - b \, ROS(t) \qquad \text{(Equation 12)}.$$

This simple linear projection may be refined as a more complex functional approximation. However, this would require a large clinical study which was out of the scope of actual study.

The measurement time period used for estimating the instantaneous $R_{OS}$ is typically chosen with respect to a given application. For example, in the case highly accurate instantaneous $SpO_2$ estimations are required and a slow dynamic response is tolerated, the statistical operation may be performed during the measurement time period corresponding to up to 120 heart beats or even more. In contrast, in the case a faster and less accurate instantaneous $SpO_2$ estimation the statistical operation can be performed during the measurement time period corresponding to up 60 heart beats or even less.

A further improvement may be achieved by replacing the statistical operator by spatiotemporal principal component analysis. Indeed, it has been shown that for PPG signals with high intrinsic time and spatial correlations, spatiotemporal principal component analysis yields improved performance in adverse highly noisy environment. Indeed, on the one hand, the multichannel sensor 1 provides $R_{OS}$ estimates from different channel locations which should be highly correlated. On the other hand, the physiological basis for pulse oximetry ensures that $SpO_2$ values from one heart beat to the next have high intrinsic correlations. Spatiotemporal principal component analysis (PCA) allows estimating a reliable evolution of the $R_{OS}$ values over a short time window of typically 20 to 120 sec. Finally, subsequent short term evolution profiles of the $R_{OS}$ can be combined in a windowing averaging technique as it is often achieved in speech processing (see reference 3: Deller J R, Hansen J H, Proakis J G (1999) Discrete-time processing of speech signals. Wiley-IEEE Press).

While the invention may be susceptible to various modifications and alternative forms, specific embodiments have been shown by way of example in the drawings and have been described in detail herein. However, it should be understood that the invention is not intended to be limited to the particular forms disclosed. Indeed, the monitoring device and the method disclosed herein may not only be applied to measurements and estimation of $SpO_2$, but may also be utilized for the measurement and/or analysis of other blood constituents in blood. For example, using the same, different, or additional wavelengths, the present monitoring device and the method can be utilized in conjunction with the measurement and/or analysis of blood constituent concentration comprising oxyhemoglobin, reduced-hemoglobin, carboxyhemoglobin (SpCO), methemoglobin (SpMet), or a combination of any of them. An example of combination of blood constituent concentrations is SpO2, defined as the ratio of oxyhemoglobin concentration over total hemoglobin concentration.

An ambulatory validation according to a first example was conducted using the monitoring device of FIG. 2. The first conventional finger clip sensor 8 was a NELLCOR N-595 combined with OxiMax finger-clip. The second conventional finger clip sensor 9 was a BIOPAC finger-clip transducer TSD123 AC connected to BIOPAC MP150 acquisition platform. The $SpO_2$ estimations obtained with the multichannel sensor 1 were compared to the ones obtained with the two finger-clip sensors. The two finger-clip sensors 8, 9 used here were chosen for the cross-validation procedure because of their reliability and the ease to ensure no motion at this sensor location. The validation follows the procedure for non-invasive laboratory testing on healthy volunteers of the ISO9919 international standard for Medical electrical equipment and particular requirements for the basic safety and essential performance of pulse oximeter equipment for medical use. Also visible in FIG. 2 is the ECG sensor 5 (BIOPAC).

Ten male volunteers, non-smokers, 25-54 years old, took part in this validation. Informed consent to induced hypoxia was obtained from each patient in resting supine position with a gradual breathe down protocol for $SpO_2$ values ranging from 100 to 70%. A non re-breathing system 11 attached to an oxygen ($O_2$)/Nitrogen ($N_2$)/Air gas delivery apparatus (AltiTrainer, SMTEC SA) provided the hypoxic gas mixture to the volunteer, via a facemask held in place by a fabric elastic head cradle.

$SpO_2$ estimation provided by the method disclosed above has been compared to the $SpO_2$ values of the reference devices, and the performances evaluated on the basis of the average means square error (AMSE), the bias, and the percentage of time the absolute relative error was <0.3%. Table 1 below summarizes the performance evaluation.

Figure 4:
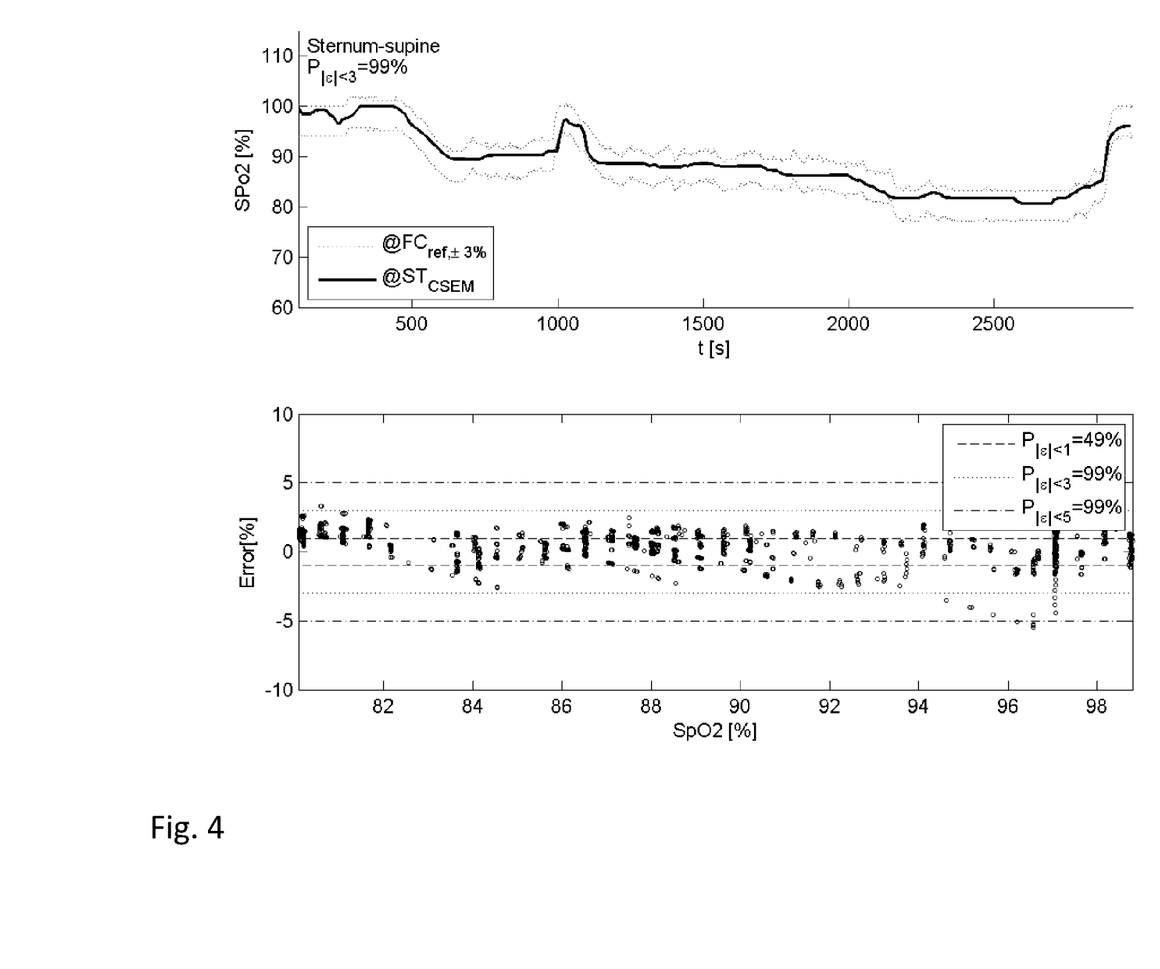
FIGS. 4 and 5 show a plot of $SpO_2$ estimation (upper graph) and relative error (lower graph) for different measurement examples.
Figure 5:
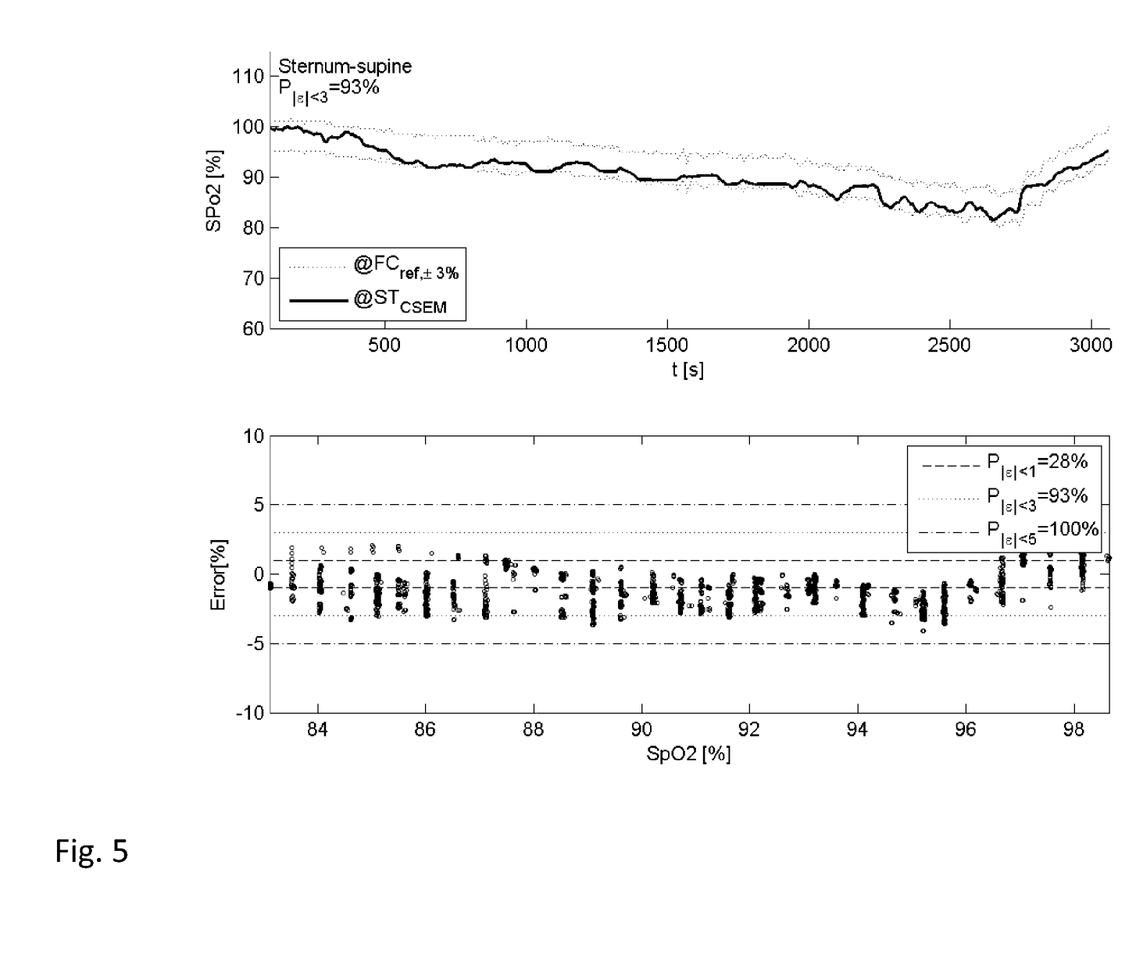

Similar performances have been observed in nine out of the ten tested subjects. FIG. 4 reports the results for one of the subjects (subject 5) where the method showed similar performances. FIG. 5 reports the results of another subject (subject 10), where the method provided poor $SpO_2$ estimation. More particularly, the upper graphs of FIGS. 4 and 5 plot the $SpO_2$ estimation obtained with the multichannel sensor 1 (thick line, noted as "@$ST_{CSEM}$" in the legend). Confidence intervals determined by the measurements with the conventional finger-clip sensors 8, 9 are shown by the dotted lines (denoted "@$FC_{ref,\pm3\%}$" in the legend). The relative error (Error in %) with confidence intervals for the $SpO_2$ estimation obtained with the multichannel sensor 1, first and second conventional finger-clip sensors 8, 9 are shown in the bottom graphs of FIGS. 4 and 5 by the circles. In the bottom graphs of FIGS. 4 and 5, the lines represent the different confidence intervals as described in the corresponding legends. It can be noticed that when the algorithm poorly estimates the $SpO_2$ (subject 10) it also indicates the low reliability of the estimation (see FIG. 5).

TABLE 1

Evaluation results of our algorithm

| Subject | AMSE | bias | % abs err <3% |
|---|---|---|---|
| 1 | 1.3555 | 0.1137 | 95.4395 |
| 2 | 1.9861 | −0.2712 | 88.9400 |
| 3 | 1.0477 | 0.1905 | 99.1556 |
| 4 | 2.0555 | 1.5006 | 85.4915 |
| 5 | 1.2782 | 0.0516 | 97.5844 |
| 6 | 1.5020 | 0.8062 | 98.4399 |
| 7 | 1.9408 | −1.3643 | 87.2347 |
| 8 | 2.0642 | −0.0779 | 85.9316 |
| 9 | 1.8069 | −1.5085 | 95.0396 |
| 10 | 2.7272 | 1.6410 | 69.4551 |

In contrast to classical frequency based pulse oximetry algorithms using FFT or DCT, the disclosed method requires computational load that is highly diminished since only one component is used while frequency resolution and associated projection bandwidth is even improved. Indeed, whereas in FFT or DCT frequency resolution is determined by the order of the applied transform, the method disclosed herein provides the exact location of the principal frequency component as the short-term mean of the instantaneous heart rate. Moreover, the projection bandwidth which is determined by the type and length of the pre-window can be adjusted depending on the relative levels of movement artifacts and large-band background noise, and/or the level of accuracy required in $SpO_2$ estimation.

REFERENCE NUMBERS

1 multichannel sensor
2 emitter
3 first radiation source
4 second radiation source
5 receiver
6 motion sensor
7 ECG electrodes
8 first conventional finger clip sensor
9 second conventional finger clip sensor
10 strap band
11 non re-breathing system
13 chest band
14 ECG ground electrode
15 filtering, band-pass 8 to 17 Hz
16 HR estimation through R-wave location
17 activity processing
18 window design
19 FIR filtering
20 pre-windowing
21 projecting on a principal frequency component
22 discarding non-reliability projected PPG signals
23 instantaneous $R_{OS}$ estimation
24 instantaneous $SpO_2$ estimation
ADC analog-to-digital converter
CV cardio-synchronous
FIR finite impulse response
PC principal frequency component
PPG photoplethysmographic
$W_{len}$ window length

The invention claimed is:
1. Method for estimating a hemoglobin-related blood constituent concentration of a user under low perfusion conditions:
measuring a plurality of photoplethysmographic (PPG) signals by using a spectrophotometry-based monitoring device comprising a multichannel sensor formed from a plurality of channels, each PPG signal being measured by one of the channels;

measuring a cardio-synchronous (CV) signal by using a cardiovascular sensor of the spectrophotometry-based monitoring device; and using a signal processor configured for:
  detecting an instantaneous heart rate and determining a heart rate variability from the CV signal;
  for each detected heart rate, determining projected PPG signals by projecting the measured PPG signals multiplied by a window function on a principal frequency component, and determining a magnitude of the projected PPG signals as the sum of the projected PPG signals;
  selecting reliable projected PPG signals, wherein reliable projected PPG signals are projected PPG signals which have a predetermined magnitude and a predetermined phase and/or coherence between the PPG signals and the principal frequency component;
  estimating a value of said blood constituent concentration from the magnitude of said reliable projected PPG signals selected over a predetermined time period;
  said window function having a window length which is adjusted at each detected heart rate according to the determined heart rate variability; and
  the frequency of said principal frequency component being estimated by averaging the heart rate over the window length.

2. The method according to claim 1, wherein said blood constituent concentration comprises blood oxygen saturation, carboxyhemoglobin, met-hemoglobin, or a combination of any of them.

3. The method according to claim 1, wherein the principal frequency component is a harmonic component, said principal frequency component's phase being determined by the instantaneous heart rate and said principal frequency component's frequency being determined by the averaged heart rate.

4. The method according to claim 1, wherein the principal frequency component is the fundamental wavelet of a wavetable oscillator, said principal frequency component's phase being determined by the instantaneous heart rate and said principal frequency component's frequency being determined by the averaged heart rate.

5. The method according to claim 1, wherein said averaging the heart rate comprises determining the mean heart rate value of heart rate detected prior to the instantaneous heart rate, over the whole window length.

6. The method according to claim 1, wherein said predetermined coherence is equal or above 0.7.

7. The method according to claim 1, wherein the monitoring device further comprises a motion sensor or measuring a motion signal, and wherein the method further comprises extracting a motion frequency from the motion signal.

8. The method according to claim 7, wherein the window function is designed according to the extracted motion frequency.

9. The method according to claim 8, wherein for the motion artifacts being smaller than large-band background noise, the window function has maximal attenuation of lateral lobes.

10. The method according to claim 9, wherein the window function is a Hanning window or a Kaiser window.

11. The method according to claim 10, wherein for the motion artifacts being larger than large-band background noise, the window function yields an equivalent frequency response having zeros at the motion frequency and motion frequency harmonics.

12. The method according to claim 11, wherein the window function is a rectangular window.

13. The method according to claim 3, wherein the phase of said principal frequency component is determined by the corresponding instantaneous R-wave location, or instantaneous heart rate, on a CV signal delivered by an ECG-based sensor.

14. The method according to claim 1, wherein each of said plurality of channels comprises at least two radiation sources, each radiation source emitting radiation at a wavelength, and the wavelength of each of said radiation sources is selected in accordance with the hemoglobin-related blood constituent concentration to be estimated.

15. Monitoring device for estimating a hemoglobin-related blood constituent concentration in tissue under low perfusion of a user comprising:
  a multichannel sensor formed from a plurality of photoplethysmographic (PPG) sensor channels, each PPG sensor channel configured to measure a PPG signal;
  a cardiovascular sensor configured to measure a cardio-synchronous (CV) signal;
  and a signal processor configured to:
    detect an instantaneous heart rate and determine a heart rate variability from the CV signal;
    for each detected heart rate, determining projected PPG signals by projecting the measured PPG signals multiplied by a window function on a principal frequency component, and determining a magnitude of the projected PPG signals as the sum of the projected PPG signals;
    select reliable projected PPG signals, wherein reliable projected PPG signals are projected PPG signals which have a predetermined magnitude and a predetermined phase and/or coherence between the PPG signals and the principal frequency component;
    estimate a value of said blood constituent concentration from the magnitude of said reliable projected PPG signals selected over a predetermined time period;
    said window function having a window length which is adjusted at each detected heart rate according to the determined heart rate variability; and
    the frequency of said principal frequency component being estimated by averaging the heart rate over the window length.

16. The monitoring device according to claim 15, further comprising a motion sensor for measuring a motion signal.

17. The monitoring device according to claim 15, wherein each of said plurality of channels comprises an emitter containing a first and second radiation source emitting at the red and infrared wavelengths, respectively, and a receiver for receiving optical radiation emitted by the emitter.

18. The monitoring device according to claim 15, wherein said cardiovascular sensor is an ECG sensor and the CV signal is a surface ECG signal.

19. The monitoring device according to claims 15, wherein said cardiovascular sensor is a PPG sensor and the CV signal is a PPG signal.

20. The monitoring device according to claim 15, wherein each of said plurality of channels comprises at least two radiation sources, each radiation source emitting radiation at a wavelength, and the wavelength of each of said radiation sources is selected in accordance with the hemoglobin-related blood constituent concentration to be estimated.

21. Method for estimating a hemoglobin-related blood constituent concentration of a user under low perfusion conditions, comprising:

measuring a plurality of photoplethysmographic (PPG) signals by using a spectrophotometry-based monitoring device comprising a multichannel sensor formed from a plurality of channels, each PPG signal being measured by one of the channels;

measuring a cardio-synchronous (CV) signal by using a cardiovascular sensor of the spectrophotometry-based monitoring device; and using a signal processor configured for:

detecting an instantaneous heart rate and determining a heart rate variability from the CV signal;

for each detected heart rate, determining projected PPG signals by projecting the measured PPG signals multiplied by a window function on a principal frequency component, and determining a magnitude of the projected PPG signals as the sum of the projected measured PPG signals;

selecting reliable projected PPG signals, wherein reliable projected PPG signals are projected PPG signals which have a magnitude at least twice the noise floor, or a coherence between the PPG signals and the principal frequency component having a value equal or above 0.7, or the phase being less than a maximal angle resulting in a linear phase relationship between the phase and a maximally elapsed time between the occurrence of the heart beat and PPG pulse wave at the sensor location;

estimating a value of said blood constituent concentration from the magnitude of said reliable projected PPG signals selected over a predetermined time period;

said window function having a window length which is adjusted at each detected heart rate according to the determined heart rate variability; and the frequency of said principal frequency component being estimated by averaging the heart rate over the window length.

22. The method according to claim 21, wherein each of said plurality of channels comprises at least two radiation sources, each radiation source emitting radiation at a wavelength, and the wavelength of each of said radiation sources is selected in accordance with the hemoglobin-related blood constituent concentration to be estimated.

* * * * *